United States Patent
Rohwer

(10) Patent No.: US 12,241,092 B2
(45) Date of Patent: Mar. 4, 2025

(54) PRODUCTS OF MANUFACTURE AND METHODS TO ENRICH FOR AND ISOLATE VIRUSES OR PHAGES CAPABLE OF TARGETING SPECIFIC MICROBES

(71) Applicant: San Diego State University (SDSU) Foundation, San Diego, CA (US)

(72) Inventor: Forest Rohwer, San Diego, CA (US)

(73) Assignee: San Diego State University (SDSU) Foundation, San Diego, CA (US)

(*) Notice: Subject to any disclaimer, the term of this patent is extended or adjusted under 35 U.S.C. 154(b) by 833 days.

(21) Appl. No.: 16/761,037

(22) PCT Filed: Nov. 2, 2018

(86) PCT No.: PCT/US2018/058879
§ 371 (c)(1),
(2) Date: May 1, 2020

(87) PCT Pub. No.: WO2019/090034
PCT Pub. Date: May 9, 2019

(65) Prior Publication Data
US 2021/0180030 A1 Jun. 17, 2021

Related U.S. Application Data

(60) Provisional application No. 62/581,309, filed on Nov. 3, 2017.

(51) Int. Cl.
*C12N 7/00* (2006.01)
*A01N 63/40* (2020.01)
*A61K 35/76* (2015.01)
*C12N 7/02* (2006.01)

(52) U.S. Cl.
CPC ............... *C12N 7/00* (2013.01); *A01N 63/40* (2020.01); *A61K 35/76* (2013.01); *C12N 7/02* (2013.01); *C12N 2795/00021* (2013.01); *C12N 2795/00031* (2013.01); *C12N 2795/00032* (2013.01); *C12N 2795/00051* (2013.01)

(58) Field of Classification Search
CPC ............ C12N 7/00; C12N 2795/00021; C12N 2795/00031; C12N 2795/00032; C12N 2795/00051; A01N 63/40; A61K 35/76
See application file for complete search history.

(56) References Cited

PUBLICATIONS

Naureen et al., Acta Biomed, 2020; vol. 91, Supplement 13: e2020024, pp. 1-13. (Year: 2020).*
The printout of BD Tryptic Soy Broth, downloaded on Jan. 27, 2023 from https://www.bd.com/resource.aspx?IDX=30505#:~:text=BD%20Tryptic%20Soy%20Broth%20(Soybean,that%20are%20not%20excessively%20fastidious (Year: 2023).*
McLaughlin et al., Journal of Environmental Quality, 2006, 35(2): 522-528 (Year: 2006).*
Howard et al., Virulence, 2012, 3:3, 243-250. (Year: 2012).*
Young, International Search Report and Written Opinion for PCT/US2018/058879, Jan. 22, 2019.
Sulakvelidze et al, "Bacteriophage Therapy" Antimicrobial Agents and Chemotherapy, Mar. 2001, v 15, n 3, p. 649-659.
Schooley et al., "Development and Use of Personalized Bacteriophage-Based Therapeutic Cocktails To Treat a Patient with a Disseminated Resistant Acinetobacter baumannii Infection" Antimicrobial Agents and Chemotherapy, Oct. 2017, v 61, n 10, p. 1-14.
Young, International Preliminary Report on Patentability for PCT/US2018/058879, May 14, 2020.

* cited by examiner

*Primary Examiner* — Qing Xu
(74) *Attorney, Agent, or Firm* — Gregory P. Einhorn; Greer, Burns & Crain, Ltd.

(57) ABSTRACT

In alternative embodiments, provided are products of manufacture and kits, and methods, to enrich for and/or isolate microbes such as viruses and/or phages capable of targeting, e.g., binding to, targeting, and/or killing or otherwise making non-viable or non-pathogenic, specific or desired microbes such as bacteria. In alternative embodiments, provided are products of manufacture comprising: a virus and/or a phage (a bacteriophage). In alternative embodiments, provided are products of manufacture and kits containing a virus and/or a phage (a bacteriophage) enriched for, selected for or isolated by a method as provided herein, or a microbe containing a virus and/or a phage (a bacteriophage) enriched, selected for and/or isolated by a method as provided herein.

22 Claims, No Drawings

PRODUCTS OF MANUFACTURE AND METHODS TO ENRICH FOR AND ISOLATE VIRUSES OR PHAGES CAPABLE OF TARGETING SPECIFIC MICROBES

RELATED APPLICATIONS

This U.S. National Phase Patent Application claims benefit of priority under 35 U.S.C. § 371 to Patent Convention Treaty (PCT) International Application number PCT/US2018/058879, filed Nov. 2, 2018, which claims the benefit of priority to U.S. Provisional Application Ser. No. (USSN) 62/581,309, filed Nov. 3, 2017. The aforementioned applications are expressly incorporated herein by reference in their entirety and for all purposes.

TECHNICAL FIELD

This invention generally relates to infectious diseases and microbiology. In alternative embodiments, provided are products of manufacture and kits, and methods, to enrich for and/or isolate microbes such as viruses and/or phages capable of interacting with, e.g., binding to, targeting, and/or killing or otherwise making non-viable or non-pathogenic, specific or desired microbes such as bacteria.

BACKGROUND

Any macroorganism (macrobe; e.g., animal or plant) is a holobiont (Rohwer 2002), which includes the viruses and cellular microbes that preferentially associated with the macrobe. Most of the macrobe-microbe interactions in animals occur at mucosal-like surfaces, characterized by complex protein-carbohydrate structures like mucus, cellulose, et cetera. Microbes also form complex communities with surfaces ranging from shower walls to inorganic matrices like soil to the enamel of teeth. In all cases, these microbe-surface interactions involve molecular mechanisms to attach the viral and microbial communities, as well as nutrient gradients of nutrients, oxygen, redox and pH.

Obesity and malnutrition of humans is, in part, a result of microbial and viral activities in the large intestine. In the case of obesity, too many bacteria cells belonging to the *Firmicutes* phylum are associated with weight gain and the inability to lose weight. Antibiotics are not particularly useful to treat this pathology because they act relatively indiscriminately (that is, killing the *Firmicutes* will also lead to a decrease in the microbes that are not involved in the pathogenesis and/or are actually helpful to obtaining the desired phenotype). Similarly, extremely targeted approaches like endotoxins, antibodies, et cetera are too narrow to decrease the relative abundance of a phylum like *Firmicutes*.

SUMMARY

In alternative embodiments, provided are methods for isolating, enriching for or selecting for a virus and/or a phage (a bacteriophage) capable of targeting, binding to, changing the phenotype of or killing or otherwise making non-viable or non-pathogenic a microbe, comprising:
(a) creating or providing a microbial niche or microenvironment having one or a plurality of microbes, or a community of microbes or a complex community of different microbes;
(b) inoculating the microbial niche or microenvironment with the virus or the phage, or inoculating with a plurality of the viruses or phages;
(c) culturing the inoculated microbial niche or microenvironment under (optionally changing) conditions wherein one or more new generations of virus and/or phage are produced, generated, enriched for or selected for, wherein optionally the production, generation or selection of the one or more new generations of virus and/or a phage result in generating, enriching for or selecting: a desired (changed) phenotype of the microbe (or the plurality of microbes, the community of microbes or the complex community of different microbe); a virus and/or a phage capable of killing or otherwise making non-viable or non-pathogenic the microbe (or the plurality of microbes, the community of microbes or the complex community of different microbe); a desired (changed) microbial niche or microenvironment; or, a switch between one state or condition of the niche or microenvironment to another state or condition.

In alternative embodiments, the virus or phage or a plurality of viruses or phages used for inoculation is isolated from a natural source or an in vivo source, or an artificial environment or an in vitro source. In alternative embodiments, the microbe is a bacteria (a bacterium), or a complex community of different microbes comprising a virus and a phage capable of infecting the same microbe, and optionally the bacteria is a member of or derived from the genus or phylum *Clostridium* or *Firmicutes*.

In alternative embodiments, the microbial niche or microenvironment is or comprises: a mucosal-like surface, niche or microenvironment; a niche or microenvironment characterized by or comprising complex protein-carbohydrate structures; or, a niche or microenvironment comprising mucus and/or cellulose or comprising a plurality of components of mucus and/or cellulose. In alternative embodiments, the microbial niche or microenvironment is or comprises: a tooth or an enamel (or a tooth) surface; a dentin, a cementum or a root surface of a tooth; or a bone surface. In alternative embodiments, the microbial niche or microenvironment is or comprises, or is adhered or otherwise attached to or interactive with: an inorganic, a metal, a plastic, a graphite, a polymeric, a ceramic or a porcelain surface, for example, a medical or dental implant surface, or a medical device surface, including for example a catheter, an artificial value, a stent and the like. In alternative embodiments, the microbial niche or microenvironment is or comprises: a natural niche or microenvironment, wherein optionally the natural niche or microenvironment comprises feces, a soil, a sand, a bog or a wetland sediment, or a niche or microenvironment from an animal or a human, optionally a mouth or a gut. In alternative embodiments, the microbial niche or microenvironment is or comprises: a man-made or unnatural niche or microenvironment, wherein optionally the man-made or unnatural niche or microenvironment comprises sewage or other animal waste, an industrial waste, an agricultural waste, a plant or a crop waste or a bagasse, a plant source (optionally a harvested food, e.g., grain, or a stored grain, and the like). In alternative embodiments, the microbial niche or microenvironment is or comprises: in in vivo niche or microenvironment, wherein optionally the in vivo niche or microenvironment comprises or is, or substantially is similar to, an animal: gut or rumen, skin, nasal, ocular or periocular or an oral or perioral environment, tissue niche or microenvironment, or a wound niche or microenvironment, wherein optionally the animal is a human.

In alternative embodiments, the methods further comprise isolating and/or characterizing the enriched for virus or phage, and optionally the generated, enriched for or selected virus or phage is isolated or characterized by fumigating or otherwise treating the inoculated and cultured microbial niche or microenvironment such that only the microbes are killed, wherein optionally substantially most of the microbes or killed or rendered non-viable (and the virus or phage remain viable, or substantially viable), wherein optionally the fumigating agent comprises a chloroform or equivalent.

In alternative embodiments, the methods further comprise culturing the generated, enriched for, selected, or isolated virus or phage, or the virus or phage of the first round of culturing, for one or multiple rounds of culturing (and optionally further comprising isolation of the virus or phage after each consecutive one or multiple rounds of culturing) under the same, increasingly changed or extreme or different conditions (in the same or different niche or microenvironment) to generate, enrich for or select for a different or modified, e.g., a desired, virus or phage phenotype.

In alternative embodiments, provided are methods for changing or modifying the phenotype of or killing or otherwise rendering non-viable or non-pathogenic a microbe comprising contacting or infecting the microbe with a virus and/or phase enriched by a method as provided herein, or inserting or injecting (into the microbe) a virus and/or phase enriched by a method as provided herein, or inserting or injecting a genome (or a portion of the genome, or a derivative or reproduction of all or some of the genome) of the virus and/or phage, into the microbe.

In alternative embodiments, provided are methods for facilitating the establishment of or generating a modified, or a desired, microbial niche or microenvironment, or manipulating a switch between one state or condition of the niche or microenvironment to another state or condition, comprising:
  contacting or infecting the microbe with a virus and/or phase enriched by a method as provided herein, or inserting or injecting a virus and/or phase enriched by a method as provided herein, or a genome (complete or partial) of the virus and/or phage, into the microbe or the microbial niche or microenvironment,
  wherein the virus and/or phage has been enriched for its ability to: generate a modified or a desired microbial niche or microenvironment; or, manipulate a switch between one state or condition of the niche or microenvironment to another state or condition,
  wherein optionally the switch between one state or condition of the niche or microenvironment to another state or condition comprises a switch from an anaerobic to an aerobic niche or microenvironment, or a switch from an aerobic to an anaerobic niche or microenvironment,
  or optionally the switch between one state or condition of the niche or microenvironment to another state or condition comprises a switch from one redox state, or one pH gradient, to another redox state or pH gradient,
  or optionally the switch between one state or condition of the niche or microenvironment to another state or condition comprises generation of a changed niche or microenvironment having: more or less of a targeted microbe; and/or, an altered phenotype of a targeted microbe, wherein optionally the niche or microenvironment is a human gut, or an animal rumen, and the changed niche or microenvironment has less of a targeted bacteria, e.g., has less bacteria of the genus or phylum *Clostridium* or *Firmicutes*.

In alternative embodiments, provided are products of manufacture comprising: a virus and/or a phage (a bacteriophage) enriched, selected for and/or isolated by a method as provided herein; or a microbe (e.g., a bacteria) comprising or having contained therein a virus and/or a phage (a bacteriophage) enriched by, selected for or isolated by a method as provided herein, or having all or a portion of the genome of a virus and/or a phage (a bacteriophage) enriched by, selected for or isolated by a method as provided herein.

In alternative embodiments, the product of manufacture is fabricated or manufactured as a pharmaceutical composition or a formulation, optionally a pharmaceutical composition or a formulation for enteral or parenteral delivery, or for oral delivery, and optionally the pharmaceutical composition or formulation is a tablet, a capsule, a geltab, a pill, a liquid, a gel, a topical, a paste, a powder, a suppository, an implant, a liposome, a particle or nanoparticle, an aerosol or a spray, or the pharmaceutical composition or formulation is lyophilized.

In alternative embodiments, products of manufacture as provided herein, or a virus and/or a phage (a bacteriophage) enriched, selected for and/or isolated by a method as provided herein, are used in manufacturing a medicament, optionally for manufacturing a medicament for treating or ameliorating, or decreasing the symptoms or delaying the onset of, or preventing, a disease, infection or condition, wherein the disease, infection or condition is or comprises obesity, a metabolic syndrome, heart disease, stroke, high blood pressure, diabetes or pre-diabetes, of an infection by a *Clostridium*, optionally a *Clostridium difficile*.

In alternative embodiments, provided are products of manufacture for use in treating or ameliorating, or decreasing the symptoms or delaying the onset of, or preventing, a disease, infection or condition, wherein the disease, infection or condition is or comprises obesity, a metabolic syndrome, heart disease, stroke, high blood pressure, diabetes or pre-diabetes, of an infection by a *Clostridium*, optionally a *Clostridium difficile*, wherein the product of manufacture comprises a product of manufacture as provided herein, or a virus and/or a phage (a bacteriophage) enriched, selected for and/or isolated by a method as provided herein.

The details of one or more exemplary embodiments of the invention are set forth in the description below. Other features, objects, and advantages of the invention will be apparent from the description and drawings, and from the claims.

All publications, patents, patent applications cited herein are hereby expressly incorporated by reference for all purposes.

DETAILED DESCRIPTION

In alternative embodiments, products of manufacture and methods provided herein take advantage of the natural ecological complexity of viral and microbial interactions to make and/or enrich for and optionally also isolate viral and phage strains, species and communities that will be used to sculpt and modify these ecosystems.

In alternative embodiments, provided are products of manufacture and kits, and methods, to enrich for and/or isolate viruses and/or phages (including groups of viruses and/or phages) capable of targeting, e.g., binding to, targeting, and/or killing or otherwise making non-viable or non-pathogenic, specific or desired microbes such as bacteria. In alternative embodiments, provided are products of manufacture and methods used to select for or enrich for and/or isolate (and then optionally characterize) viruses and/or phages (including groups of viruses and/or phages) in microbes, including complex communities of microbes that can mimic a natural environment (e.g., a gut) in an animal such as a human or in nature, or viruses and/or phages capable of modifying a complex communities of microbes or the phenotype of the microbes found therein.

In alternative embodiments, once enriched for, optionally characterized, and/or isolated, these viruses and/or phages (including groups of viruses and/or phages) are used to manipulate the targeted microbes, e.g., the cellular communities (e.g., complex communities of microbes). For example, in alternative embodiments, the enriched for and/or isolated viruses and/or phages (including groups of viruses and/or phages) are used to create desired microbial phenotypes or modified cellular communities (e.g., modify complex communities of microbes). In alternative embodiments, the enriched for and/or isolated viruses and/or phages (including groups of viruses and/or phages) are used to target and neutralize or kill targeted cellular communities (e.g., complex communities of microbes, e.g., bacteria).

In alternative embodiments, once enriched for, optionally characterized, and/or isolated, these viruses and/or phages (including groups of viruses and/or phages) are used to facilitate or effect the establishment of or generate or manipulate a switch between anaerobic and aerobic niches (e.g., oxygen gradients), redox states, pH gradients, and the like in an artificial (e.g., in vitro), an in vivo-like or an in vivo community of microbes.

In alternative embodiments, once enriched for, optionally characterized, and/or isolated, these viruses and/or phages (including groups of viruses and/or phages) are used (e.g., in vivo) to target and/or kill or neutralize (or otherwise change the phenotype of) a microbe or a community of targeted microbes such as bacteria, e.g., to a non-toxic phenotype or to an altered phenotype. For example, in one embodiment an enriched for and/or isolated virus or phase or a selected for or enriched group of viruses and/or phages are used to manipulate a microbial community or communities ex vivo or in vivo in an individual in need thereof, such as a human, to create or facilitate the establishment of or phenotype switching of microbes (e.g., *Clostridium* or *Firmicutes*), e.g., to switch the individual from one phenotype to another, e.g., to switch the individual to: a lean from an obese phenotype; or, a non-pathogenic phenotype from a pathogenic phenotype. In this exemplary embodiment, the process selects for or enriches for viruses and/or bacteriophage (phage) that drive a cellular community towards the desired phenotype of including lowering to total amount of viable *Clostridium* or *Firmicutes* in the gut, e.g., the gut of a human, where in alternative embodiments this comprises killing or otherwise making non-viable or non-pathogenic, or decreasing the viability of the *Clostridium* or *Firmicutes* population in the gut. In alternative embodiments, the enriched for, selected for and/or isolated phage and/or viruses indirectly or directly kill or decrease the viability of the *Clostridium* or *Firmicutes* population in the gut, e.g., by directly infecting members of the *Clostridium* or *Firmicutes* population.

In alternative embodiments, methods provided herein further comprise culturing the isolated virus or phage, or the microbe of the first round of culturing, for one or multiple rounds of culturing (and optionally further comprising isolation of the virus or phage after each consecutive one or multiple rounds of culturing) under the same, increasingly changed or extreme or different conditions (in the same or different niche or microenvironment) to generate, enrich for or select for the desired or a desired virus or phage phenotype, e.g., a new virus or phage, or a complex virus and/or phage population, capable of killing or otherwise making non-viable or non-pathogenic, or decreasing the viability of the *Clostridium* or *Firmicutes* population in the gut. Viral and/or phage communities that facilitate the switching from an obese or a malnutrition phenotype to a normal or a healthy phenotype are enriched for and isolated using this approach. Similarly, viral communities that stabilize a normal or a healthy phenotype can be isolated using this approach.

In alternative embodiments, in practicing methods as provided herein, conditions for desired and undesired cellular microbial communities are produced that create various defined microenvironments and niches, e.g., through biological activity of the microbial cellular communities or by the interaction of the microbial cellular community with the created or defined microenvironment or niche. For example, in one embodiment, cellular microbial communities are inoculated into tubes or other devices, like anaerobic fermenters, that encourage the communities to set up gradients of nutrients, oxygen, redox, pH, et cetera.

A specific example is: methods as provided herein comprise use of a so-called Winogradsky column or equivalents (see, e.g., Babcsanyi et al, FEMS Microbiol Ecol. 2017 Aug. 1;93(8); Estaban et al, PLoS One 2015 Aug. 6;10(8)), where this column is used to create a miniature ecosystem, e.g., to create an in vitro environment where conditions for culturing cellular microbial communities are set up (also called "niche building"). These niche-building conditions can be based on or can be similar to (or substantially similar to) niches or microenvironments found in or on e.g., diseased or healthy (e.g., normal or average) tissues or natural surfaces, or non-natural surfaces in or on an individual, including but not limited to, e.g., small and large intestines, teeth, plant roots, wounds (e.g., diabetic wounds), infected tissue environments, sinuses, biofilms, implants, pins, valves, stents, catheters, and the like. In alternative embodiments, the so-called "niche building" process comprises or is followed by using pH indicators, oxygen indicators, redox indicators, sequencing and other indicators. The media can be natural, like sea- or drinking water, or human formulated (e.g., synthetic or artificial), like Artificial Sputum Media, Luria Broth, and the like.

In one embodiment, a Winogradsky column or equivalent that is used comprises a media or environment that is chemically formulated to match a particular niche or microenvironment, e.g., a tissue, tooth or organ niche or microenvironment, e.g., a niche or microenvironment comprising (or substantially similar to) a lung sputum. Included in this exemplary media: are electron acceptors and donor, including iron and organic carbon, nitrogen compounds, amino acids, buffers, and other salts. When microbial communities are placed in this media and loaded in the Winogradsky column or equivalent, nutrient, oxygen, redox and pH gradients are established.

In alternative embodiments, the conditions for culturing microbes (before and/or after inoculation by virus or phage), and/or the virus and/or phage (which can optionally comprise a Winogradsky column or equivalent) include media and/or surfaces, wherein the surfaces can comprise a natural surface, e.g., a mucus, cellulose, enamel, bone, and the like, or a non-natural surface such as an implant (e.g., tooth or ocular), pin, valve, stent, catheter and the like. Addition of the surfaces to this process targets viral and/or phage and microbial behaviors that increase hunting, in vivo movement, attachment and/or insertion into the microbe, and the like, to or related to these surfaces, e.g., as described in Barr et al. (2016; PNAS), where we showed that phage attach to mucins by sub-diffusion. The sub-diffusion increases phage interactions with microbial cells on mucosal surfaces. The process is mediated via specialized proteins on the virions, which we are calling BAM-Domains. A BAM-Domain is any protein structure that localizes phage to a particular surface, media, region, et cetera. Phage encoding BAM-Domain proteins will have both generalized and specialized attachment and concentration on natural and artificial surfaces. In alternative embodiments, methods provided herein take advantage of (comprise use of) BAM-Domains to enrich for and/or isolate phage that attach or adhere to any surface desired, whether natural, e.g., a microbe surface or a tooth or bone surface, or to an artificial surface, e.g., to a an implant (e.g., tooth or ocular), pin, valve, stent, catheter and the like. For example, we have used artificial mono- and polysaccharides to select for coliphage T4.

In alternative embodiments, to create conditions for culturing microbes (before and/or after inoculation by virus or phage), and/or the virus and/or phage (which can optionally comprise a Winogradsky column or equivalent), natural or artificial mucus (e.g., human mucus, e.g., mucus from lungs, optionally mucus from lungs from cystic fibrosis patients) is added media to enrich or select for viruses and/or phages, e.g., to enrich or select for viruses and/or phages that use the mucus to find cellular hosts. For example, when a coliphage T4 is added (e.g., to a Winogradsky column or equivalent), it more efficiently kills *E. coli* cells. Mechanistically, we have shown that BAM-Domains on the coliphage T4 facilitate the killing; so, in alternative embodiments, methods provided herein comprise addition of mucus, cellulose, enamel, and the like to enrich for and/or select for (and optionally also isolate) phages or viruses with these BAM-like properties.

In alternative embodiments, in practicing methods as provided herein conditions can be generated or compositions added to create or encourage or expedite efficient, faster or rapid niche formation; for example, thickening agents like agar may be added to systems, e.g., added to created microenvironments or niches, including a Winogradsky column or equivalent. Additionally, enzymes, e.g., an oxyrase (e.g., recombinant or isolated), and/or chemicals, including e.g., alternate electron acceptors and donors, that encourage the cellular communities with the desired characters also may be added to the system, e.g., added to the microenvironment or niche, including e.g., a Winogradsky column or equivalent. For example, these enzymes and/or chemicals can be added directly to system, e.g., added to the microenvironment or niche, including e.g., a Winogradsky column or equivalent; or, they can be included in a media added to the system, e.g., added to the microenvironment or niche, including e.g., a Winogradsky column or equivalent.

In alternative embodiments, the microenvironment or niche, including e.g., a Winogradsky column or equivalent, is inoculated with a phage, a virus or a mixture thereof, or complex communities thereof, to generate a viral-microbial or a phage-microbial community, e.g., from a natural, a man-made or an artificial source.

In alternative embodiments, communities and/or strains of selected for or enriched, and optionally also isolated, phages, viruses and/or microbes are passaged one to many generations and modified and/or desired phenotypes are enriched for and selected, and optionally isolated. Changes in phenotypes can be measured, e.g., using microscopy or equivalents, optotodes (e.g., an optical sensor device that optically measures a specific substance usually with the aid of a chemical transducer), electrodes, nucleic acid staining and/or sequencing, and/or metabolomic approaches.

In alternative embodiments, passages may or may not include enrichment and/or selection for different components. For example, in one embodiment, a Winogradsky column or equivalent approach for isolating viruses is used. In one exemplary embodiment, a media that resembles sputum (e.g., from humans) is constructed, including the mucus. For example, in alternative embodiments, methods as provided herein further comprise organic fumigation (e.g., using chloroform, octanol or equivalents) to remove microbes and only pass on viral and/or phage communities between generations (e.g., rounds of selection); and optionally fumigation is used between each round of selection and passage.

In alternative embodiments, the created or provided microbial niche or microenvironment having one or a plurality of microbes, or a community of microbes or a complex community of different microbes, e.g., one from a patient with a particular disease, infection or condition, is inoculated with the virus or phage or a plurality of viruses or phages. In one embodiment, a complex community of different microbes is isolated or derived from either a generalized cystic fibrosis (CF) community or a specific community one from a patient. In one embodiment, a complex community of different microbes is isolated or derived from either a Crohn's disease (CD) community or a specific community one from a patient. For the inoculation, either viruses and/or phages from a natural community, a community from a patient with the disease, infection or condition, e.g., a CF or CD community, or viruses and/or phages from another source, are added to the mixture.

In alternative embodiments: when inoculated into an air-impermeable tube opened at one end, a range of oxic-to-anoxic conditions are created as the microbes utilize the oxygen. In one embodiment, viruses or phages that kill the microbes under these conditions (e.g., oxic-to-anoxic, or anaerobic, conditions) are enriched or selected for, optionally isolated, and expanded. In one embodiment, the whole community is fumigated with chloroform, octanol or a similar solvent to kill the microbes and the viral and/or phage community is isolated. Repeating this step several times greatly enriches the desired or selected for viruses and phages. The enriched viruses and phages can be directly isolated from these mixtures or they can be further purified using conventional methods like plaque-purification.

In one embodiment, methods provided herein comprise use of fumigation to select for specific viral or phage groups and/or to eliminate the microbial cellular organism via extractions. Chloroform or a similar solvent fumigation removes microbial cells and most viruses that infect eukaryotic cells by solubilizing the membrane. Fumigation with octanol removes endotoxins, while leaving the phage and many other viruses intact.

In one embodiment, methods provided herein comprise generation of niches or microenvironments simulating *Clostridium difficile* infections; a media made from, similar to or derived from the gut flora or feces of infected patients can be used to inoculate both mucus and a microbial community from an infected patient (personalized) or as a simulated general infection (i.e., using one or more strains of *C. difficile*). In one embodiment, viruses and/or phages from a *C. difficile* community or from an exogenous source (e.g., sewage, soil) are added to the mixture, which is subsequently inoculated into air-impermeable tubes opened at one end. Microbial activity sets up the oxic-to-anoxic conditions and viruses and/or phages that kill under these conditions are expanded. Repeating this step several times greatly enriches the desired viruses and/or phages. The enriched viruses and/or phages can be directly isolated from these mixtures or further purified using conventional methods like chromatography, plaque-purification and the like.

In one embodiment, methods provided herein comprise generation of niches or microenvironments simulating metabolic syndrome, and the same general method as provided herein is used. For example, in one exemplary method, gut flora (a complex microbial or feces of patients suffering from metabolic syndrome, heart disease, stroke, high blood pressure, diabetes or pre-diabetes is inoculated into a mixture of feces-like media and mucus. A general community also can be used (i.e., strains of major microbial groups found in metabolic syndrome, heart disease, diabetes, etc. microbes). Viruses from the patient's gut flora or fecal community or from exogenous sources (e.g., sewage, soil, or specific strains such as bacteria from ATCC and the like or laboratory isolated) also can be added to the mixture, which is subsequently inoculated into air-impermeable tubes (or equivalents) opened at one end. Microbial activity sets up the oxic-to-anoxic conditions and viruses and/or phages that kill or otherwise modify microbes under these conditions are expanded. Repeating this step several times greatly enriches the desired viruses and/or phages. The enriched viruses and/or phages can be directly isolated from these mixtures or further purified using conventional methods like plaque-purification and/or chromatography and the like.

In alternative embodiments, methods as provided herein are applicable to other systems, for example, chronic wounds, rumen and other gut communities, plant associated viral-microbial communities, food sources (e.g., grain in storage) et cetera.

In alternative embodiments, methods as provided herein use a variety of different culturing, inoculating and selection variables, which can include:
1) the media,
2) degree of oxygenation, which is in turn dependent on the size of opening in tube and depth of tube,
3) polymer source, which may include sources like mucus, cellulose, lipopolysaccharide, etc. . . . , which may be personalized or generalized,
4) source of viruses and/or phages,
5) number of passages,
6) fumigation compounds and methods,
7) the culturing vehicles, e.g., Winogradsky columns or equivalent, or Winogradsky-like tubes, etc.,
8) culturing conditions (e.g., temperature, salinity, pressure, pH, oxygenation or other gas content, e.g., carbon dioxide content), and/or
9) final purification methods.

Products of manufacture and Kits

Provided are products of manufacture and kits for practicing methods as provided herein, including for example any type of culturing vehicle, e.g., a Winogradsky column or equivalent, or a Winogradsky-like tube, and the like, which can comprise a media (which optionally comprises any variety of enzymes and/or compounds for producing a desired microbial niche or microenvironment), and/or a microbial niche or microenvironment having one or a plurality of microbes, or a community of microbes or a complex community of different microbes; and also the virus and/or a phage for inoculation. In alternative embodiments provided are products of manufacture, e.g., pharmaceutical compositions or formulations such as tablets, liquids, gels or lyophilized formulations, comprising a virus and/or a phage made, selected for and/or isolated by a method as provided herein.

The invention will be further described with reference to the examples described herein; however, it is to be understood that the invention is not limited to such examples.

A number of embodiments of the invention have been described.

Nevertheless, it can be understood that various modifications may be made without departing from the spirit and scope of the invention. Accordingly, other embodiments are within the scope of the following claims.

What is claimed is:

1. An in vitro method for generating a virus or a bacteriophage having a modified phenotype, comprising:
    (a) generating in vitro a first microbial niche or microenvironment having one or a plurality of microbes, or having a community of microbes or having a complex community of different microbes;
    (b) inoculating in vitro into the first microbial niche or microenvironment a virus or a bacteriophage or a plurality of viruses or bacteriophages from a second microbial niche or microenvironment, thereby generating a third microbial niche or microenvironment;
    (c) culturing in vitro the third microbial niche or microenvironment for multiple rounds of culturing, wherein each additional round of culturing is carried out under culture conditions that are different from culture conditions used in a previous round of culturing, and after the multiple rounds of culturing the virus and/or bacteriophage having the modified phenotype is generated; and
    (d) isolating the virus or bacteriophage having the modified phenotype from the cultured third microbial niche or microenvironment after the multiple rounds of culturing.

2. The method of claim 1, wherein the virus or bacteriophage or plurality of viruses or bacteriophages used for inoculation in step (b) are isolated from a natural source or in vivo source.

3. The method of claim 1, wherein the virus or bacteriophage or plurality of viruses or bacteriophages used for inoculation in step (b) are isolated from an artificial environment or an in vitro source.

4. The method of claim 1, wherein the one or plurality of microbes comprises a bacterium, or the complex community of different microbes comprises a bacterium.

5. The method of claim 4, wherein the bacterium is a member of or derived from the genus *Clostridium* or phylum Firmicutes.

6. The method of claim 1, wherein the first or second microbial niche or microenvironment is a niche or microenvironment characterized by comprising complex protein-carbohydrate structures, a plurality of components of mucus, and/or cellulose.

7. The method of claim 1, wherein the first or second microbial niche or microenvironment is or comprises: a tooth, an enamel, a tooth surface, a dentin, a cementum, a root surface of the tooth, or a bone surface.

8. The method of claim 1, wherein the first or second microbial niche or microenvironment is contained in or comprises: an inorganic composition or surface, or a metal or graphite surface, or a polymeric, ceramic or porcelain surface.

9. The method of claim 1, wherein the first or second microbial niche or microenvironment comprises a microbe derived from a gut or a rumen, skin, a nasal environment, an ocular environment, or an oral environment of an animal.

10. The method of claim 9, wherein the animal is a human.

11. The method of claim 1, further comprising characterizing the isolated virus or bacteriophage having the modified phenotype.

12. The method of claim 11, further comprising enriching for the isolated virus or bacteriophage having the modified phenotype.

13. The method of claim 11, wherein the step (d) comprises isolating the bacteriophage having the modified phenotype, wherein the bacteriophage is isolated by a method comprising fumigating with a fumigating agent the cultured microbial niche or microenvironment obtained from step (c) such that only bacteriophage remains viable.

14. The method of claim 13, wherein the fumigating agent is chloroform.

15. The method of claim 1, wherein the each additional round of culturing is carried out under culture conditions, which differ from culture conditions of a previous round of culturing in that levels or gradients of nutrients, oxygen, redox potential, or pH, are changed.

16. The method of claim 1, wherein the virus or the bacteriophage having the modified phenotype is capable of killing or otherwise making a microbe non-viable or non-pathogenic.

17. The method of claim 1, wherein the first or second microbial niche or microenvironment is derived from a feces, a soil, a sand, a bog, a wetland sediment, or an animal.

18. The method of claim 17, wherein the first or second microbial niche or microenvironment derived from the animal is a niche or microenvironment derived from a mouth or a gut.

19. The method of claim 17, wherein the animal is a human.

20. The method of claim 1, wherein the first or second microbial niche or microenvironment further comprises sewage, an industrial waste, an agricultural waste, a plant waste, a plant source, a harvested food, a grain, a stored grain or bagasse.

21. The method of claim 1, wherein the first microbial niche or microenvironment having one or a plurality of microbes, or having a community of microbes or having a complex community of different microbes, is contained in a Winogradsky column, a tube or an anaerobic fermenter.

22. The method of claim 21, wherein the Winogradsky column, tube or anaerobic fermenter comprises an electron acceptor, an electron donor, a buffer, a salt, a mono- or polysaccharide, or a combination thereof.

* * * * *